United States Patent
Wang et al.

(10) Patent No.: US 12,186,020 B2
(45) Date of Patent: Jan. 7, 2025

(54) OPHTHALMOLOGICAL DEVICE

(71) Applicant: Topcon Corporation, Tokyo (JP)

(72) Inventors: Zhenguo Wang, Ridgewood, NJ (US);
Zaixing Mao, Harrison, NJ (US);
Kazuhiro Oomori, Tokyo (JP);
Makoto Fujino, Tokyo (JP)

(73) Assignee: Topcon Corporation, Tokyo (JP)

( * ) Notice: Subject to any disclaimer, the term of this patent is extended or adjusted under 35 U.S.C. 154(b) by 525 days.

(21) Appl. No.: 17/594,552

(22) PCT Filed: Apr. 24, 2020

(86) PCT No.: PCT/JP2020/017833
§ 371 (c)(1),
(2) Date: Oct. 21, 2021

(87) PCT Pub. No.: WO2020/218576
PCT Pub. Date: Oct. 29, 2020

(65) Prior Publication Data
US 2022/0175247 A1   Jun. 9, 2022

Related U.S. Application Data

(60) Provisional application No. 62/837,992, filed on Apr. 24, 2019, provisional application No. 62/837,914, (Continued)

(51) Int. Cl.
*A61B 3/15* (2006.01)
*A61B 3/12* (2006.01)

(52) U.S. Cl.
CPC ............... *A61B 3/152* (2013.01); *A61B 3/12* (2013.01)

(58) Field of Classification Search
CPC .................... A61B 3/152; A61B 3/12
(Continued)

(56) References Cited

U.S. PATENT DOCUMENTS

| 4,772,116 A | 9/1988 | Schroder et al. |
| 5,523,808 A | 6/1996 | Kohayakawa |

(Continued)

FOREIGN PATENT DOCUMENTS

| EP | 1974657 A2 | 10/2008 |
| EP | 2090224 B1 | 8/2014 |

(Continued)

OTHER PUBLICATIONS

International Search Report and Written Opinion mailed Jul. 14, 2020, in connection with International Patent Application No. PCT/JP2020/017833, filed Apr. 24, 2020, 11 pgs. (including translation).

(Continued)

*Primary Examiner* — Sharrief I Broome
(74) *Attorney, Agent, or Firm* — Chiesa Shahinian & Giantomasi PC

(57) ABSTRACT

An ophthalmologic apparatus includes: an objective lens that faces a subject's eye; an alignment light emitting unit that irradiates the subject's eye with alignment light to perform measurement of alignment between the objective lens and the subject's eye; an alignment reflection light receiving unit that receives alignment reflection light, which is a reflection of the alignment light from the subject's eye; an anterior segment camera that receives corneal reflection light; and a holder positioned between the anterior segment camera and the objective lens to hold the anterior segment camera, wherein the holder includes an imaging transmissive portion that transmits the corneal reflection light to the anterior segment camera, a first light-transmissive portion that transmits the alignment light from the alignment light emitting unit, and a second light-transmissive portion that transmits the alignment reflection light from the subject's eye.

15 Claims, 3 Drawing Sheets

Related U.S. Application Data filed on Apr. 24, 2019, provisional application No. 62/837,900, filed on Apr. 24, 2019, provisional application No. 62/837,844, filed on Apr. 24, 2019.

(58) Field of Classification Search
USPC .................................................. 351/208, 205
See application file for complete search history.

(56) References Cited

U.S. PATENT DOCUMENTS

| | | | |
|---|---|---|---|
| 5,682,224 | A | 10/1997 | Takagi et al. |
| 6,179,421 | B1* | 1/2001 | Pang ........................ A61B 3/12 |
| | | | 351/205 |
| 7,278,740 | B1 | 10/2007 | Suzuki et al. |
| 7,413,304 | B2 | 8/2008 | Suzuki et al. |
| 7,661,820 | B2 | 2/2010 | Hara et al. |
| 7,758,190 | B2 | 7/2010 | Korb et al. |
| 7,802,903 | B1 | 9/2010 | Wray |
| 7,854,510 | B2 | 12/2010 | Verdooner et al. |
| 7,988,294 | B2 | 8/2011 | Korb et al. |
| 8,591,033 | B2 | 11/2013 | Korb et al. |
| 11,058,295 | B2 | 7/2021 | Okazaki et al. |
| 2004/0212781 | A1 | 10/2004 | Mihashi et al. |
| 2007/0258043 | A1 | 11/2007 | Suzuki et al. |
| 2008/0055544 | A1* | 3/2008 | Nishio .................... A61B 3/135 |
| | | | 351/208 |
| 2008/0239239 | A1* | 10/2008 | Honda ..................... A61B 3/18 |
| | | | 351/208 |
| 2008/0309872 | A1 | 12/2008 | Hara et al. |
| 2008/0316426 | A1* | 12/2008 | Shibata .................... A61B 3/12 |
| | | | 351/206 |
| 2008/0316499 | A1 | 12/2008 | Korb et al. |
| 2010/0085540 | A1 | 4/2010 | Korb et al. |
| 2010/0097573 | A1 | 4/2010 | Verdooner et al. |
| 2010/0315591 | A1 | 12/2010 | Gratton et al. |
| 2011/0285961 | A1 | 11/2011 | Korb et al. |
| 2012/0236261 | A1* | 9/2012 | Sekiguchi ................ A61B 3/12 |
| | | | 351/206 |
| 2013/0293842 | A1 | 11/2013 | Grenon et al. |
| 2014/0240671 | A1 | 8/2014 | Korb et al. |
| 2014/0286019 | A1 | 9/2014 | Araki et al. |
| 2015/0085252 | A1 | 3/2015 | Fujimura et al. |
| 2015/0313468 | A1* | 11/2015 | Okada .................... A61B 3/113 |
| | | | 351/208 |
| 2016/0143529 | A1* | 5/2016 | Miyashita .............. A61B 3/152 |
| | | | 351/208 |
| 2019/0117064 | A1* | 4/2019 | Fletcher ............ H04M 1/72409 |
| 2019/0374100 | A1 | 12/2019 | Okazaki et al. |
| 2021/0106224 | A1 | 4/2021 | Zhou et al. |

FOREIGN PATENT DOCUMENTS

| | | | |
|---|---|---|---|
| EP | 2878259 | A1 | 6/2015 |
| JP | S61-500649 | A | 4/1986 |
| JP | H0288035 | A | 3/1990 |
| JP | H0647003 | A | 2/1994 |
| JP | H07-136120 | A | 5/1995 |
| JP | H08173385 | A | 7/1996 |
| JP | 3056799 | B | 6/2000 |
| JP | 2000216810 | A | 8/2000 |
| JP | 2000-287928 | A | 10/2000 |
| JP | 2005-168941 | A | 6/2005 |
| JP | 3896211 | B | 3/2007 |
| JP | 2008-011983 | A | 1/2008 |
| JP | 2008-246071 | A | 10/2008 |
| JP | 4624122 | B2 | 2/2011 |
| JP | 2012-55337 | A | 9/2013 |
| JP | 5651119 | B2 | 1/2015 |
| JP | 5665181 | B2 | 2/2015 |
| JP | 2016-049255 | A | 4/2016 |
| JP | 2019-025257 | A | 2/2019 |
| WO | 2008062527 | A1 | 5/2008 |
| WO | 2011066065 | A1 | 6/2011 |

OTHER PUBLICATIONS

Non-Final Rejection mailed Feb. 2, 2022, in connection with U.S. Appl. No. 16/845,747, filed Apr. 10, 2020, 9 pgs.

Notice of Reasons for Refusal mailed Nov. 14, 2023 in connection with Japanese Patent Application No. 2020-077703, 8 pgs. (including translations).

* cited by examiner

OPHTHALMOLOGICAL DEVICE

CROSS-REFERENCE TO RELATED APPLICATIONS

This application is a national stage of International Patent Application Serial No. PCT/JP2020/017833 filed Apr. 24, 2020, which claims priority to U.S. Provisional Patent Applications Nos. 62/837,992 filed Apr. 24, 2019; 62/837,914 filed Apr. 24, 2019; 62/837,900 filed Apr. 24, 2019; and 62/837,844 filed Apr. 24, 2019, the disclosures of all are incorporated herein by reference in their entirety.

TECHNICAL FIELD

The present disclosure relates to an ophthalmologic apparatus, and more particularly, to an ophthalmologic apparatus that examines states of an anterior segment and tear fluid film of a subject's eye.

BACKGROUND ART

There has been known an ophthalmologic apparatus that is used to make a diagnosis of dry eye, for example. The apparatus irradiates a cornea of a subject's eye with illumination light, and observes a state of an anterior segment and an interference image formed by a tear fluid film of the cornea of the subject's eye.

If the ophthalmologic apparatus and the subject's eye are not accurately located at predetermined positions during the diagnosis, a measurement error increases. Therefore, in general, the ophthalmologic apparatus is provided with an alignment detection system for detecting whether they are accurately located or not (Patent Document 1).

CITATION LIST

Patent Document

Patent Document 1: Japanese Patent No. 3056799

SUMMARY OF THE INVENTION

Technical Problem

However, for example, if the ophthalmologic apparatus includes an anterior segment observation optical system for taking an image of an anterior segment and a corneal measurement optical system for measuring a tear fluid film, and is able to observe, and take images of, the anterior segment and the tear fluid film, the size of the entire ophthalmologic apparatus may increase depending on how the alignment detection system, the imaging optical system, and the corneal measurement optical system are arranged.

The present disclosure has been made to solve the above-described problem, and it is therefore an object of the present disclosure to provide an ophthalmologic apparatus that is downsized, while increasing an accuracy of alignment detection.

Solution to the Problem

An ophthalmologic apparatus of the present disclosure includes: an objective lens that faces a subject's eye; an alignment light emitting unit that irradiates the subject's eye with alignment light to perform measurement of alignment between the objective lens and the subject's eye; an alignment reflection light receiving unit that receives alignment reflection light, which is a reflection of the alignment light from the subject's eye; an anterior segment camera that receives corneal reflection light; and a holder positioned between the anterior segment camera and the objective lens to hold the anterior segment camera. The holder includes an imaging transmissive portion, a first light-transmissive portion that transmits the alignment light from the alignment light emitting unit, and a second light-transmissive portion that transmits the alignment reflection light from the subject's eye.

Advantages of the Invention

The present disclosure can provide an ophthalmologic apparatus that is downsized, while increasing an accuracy of alignment detection.

DESCRIPTION OF EMBODIMENTS

First Embodiment

Figure 1:
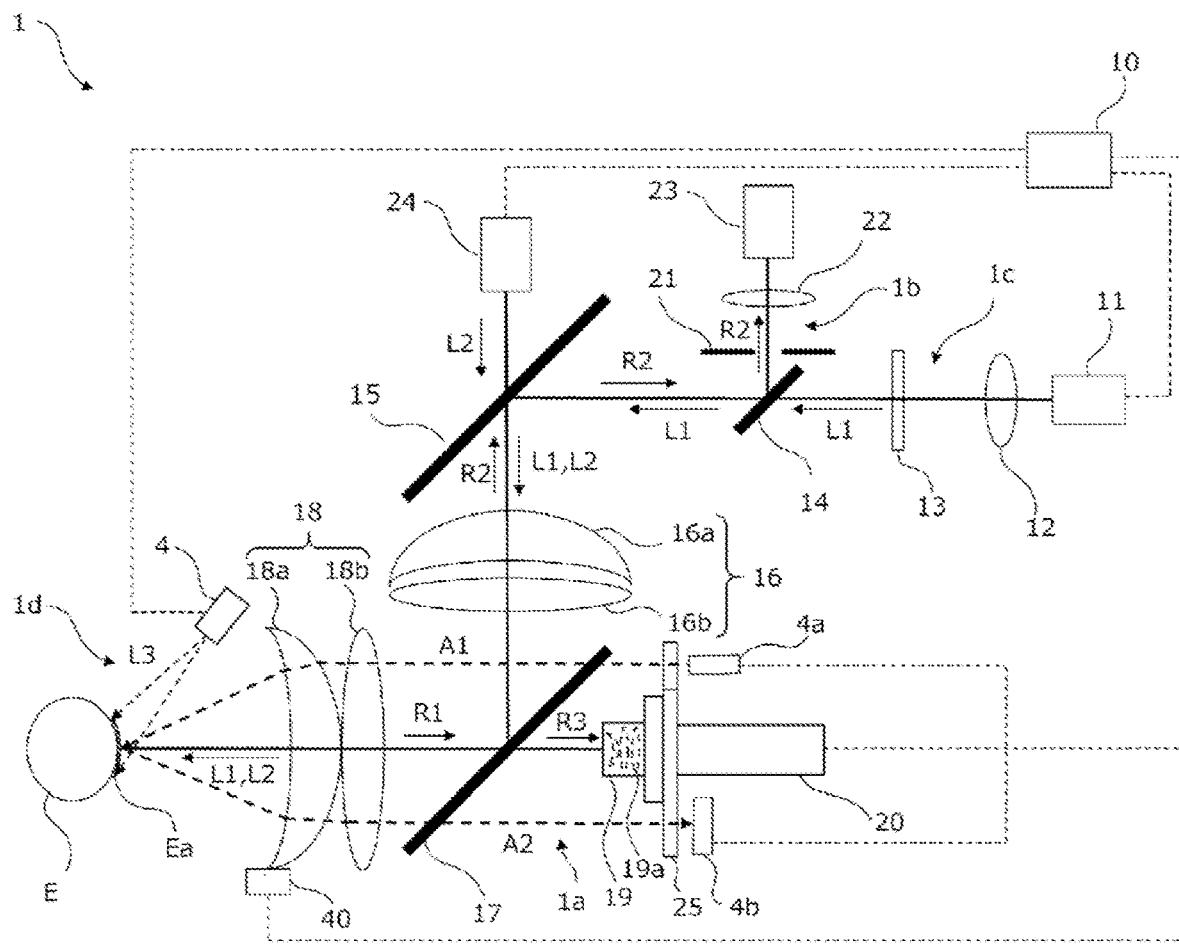
FIG. 1 is a schematic view illustrating an optical system of an ophthalmologic apparatus according to a first embodiment of the present disclosure.

FIG. 1 is a schematic view illustrating an optical system of an ophthalmologic apparatus 1 according to a first embodiment of the present disclosure. The optical system of the ophthalmologic apparatus 1 includes an anterior segment observation optical system 1a, a corneal measurement optical system 1b, a first illumination optical system 1c, and a second illumination optical system 1d.

The anterior segment observation optical system 1a includes a first lens group 18 of the present disclosure. The anterior segment observation optical system 1a includes a third half mirror 17, an imaging lens 19a, and an anterior segment camera 20 that are arranged along the direction of an optical axis of the first lens group 18.

The first lens group 18 is a so-called objective lens. In the present embodiment, the objective lens (first lens group 18) includes a plurality of lenses (18a, 18b), but the objective lens may include a single lens only. The first lens group 18 irradiates a corneal surface of a cornea Ea of a subject's eye E with illumination light L1 incident from a first illumination optical system 1c, which will be described later, via the third half mirror 17. Corneal reflection light R1, which is the reflection of the illumination light from the corneal surface, enters the first lens group 18. This corneal reflection light R1 enters the third half mirror 17 from the first lens group 18.

The third half mirror 17 reflects part of illumination light L1 incident from the first illumination optical system 1c toward the first lens group 18. Further, the third half mirror 17 allows part (R3) of the corneal reflection light R1 incident from the first lens group 18 to pass therethrough and exit therefrom toward the imaging lens 19a, and reflects further part (R2) of the corneal reflection light R1 toward a second lens group 16, which will be described later.

The imaging lens 19a allows the corneal reflection light R3 incident from the third half mirror 17 to pass therethrough and exit therefrom toward the anterior segment camera 20. The anterior segment camera 20 is relatively held by and fixed to a holder 25, which will be described later. The anterior segment camera 20 includes a complementary metal oxide semiconductor (CMOS) or charge coupled device (CCD) imaging element, and takes an image of the corneal reflection light R3 incident from the imaging lens 19a to output an imaging signal of an observation image of an anterior segment of the subject's eye E (will be hereinafter referred to as an "anterior segment observation image") to a control unit 10.

The first illumination optical system 1c includes a first illumination light source 11. The first illumination optical system 1c further includes a lens 12, a filter 13, a first half mirror 14, a second half mirror 15, and a second lens group 16 which are arranged on an optical path of illumination light L1 emitted from the first illumination light source 11. The first illumination optical system 1c shares the third half mirror 17 and the first lens group 18 with the anterior segment observation optical system 1a. In this manner, the first illumination optical system 1c forms an optical path branching from the anterior segment observation optical system 1a via the third half mirror 17.

The first illumination light source 11 emits light. The first illumination light source 11 may be, for example, a light emitting diode (LED) light source or halogen lamp which emits white light, and emits white light as the illumination light L1 toward the lens 12. Alternatively, an LED having a different wavelength, a laser light source, or a combination of them may also be used. The lens 12 allows the illumination light L1 incident from the first illumination light source 11 to exit therefrom toward the filter 13. The filter 13 adjusts the light intensity and/or wavelength distribution of the illumination light L1 incident from the lens 12, and allows the illumination light L1 thus adjusted to exit therefrom toward the first half mirror 14. Note that the LED may be a bullet-shaped LED. The LED may be replaced with a single halogen lamp or the like.

The first half mirror 14 allows part of the illumination light L1 incident from the filter 13 to pass therethrough and exit therefrom toward the second half mirror 15, and reflects part of the corneal reflection light R3 incident from the second lens group 16, which will be described later, via the second half mirror 15 toward the corneal measurement optical system 1b, which will be described later.

The second half mirror 15 and the second lens group 16 allow the illumination light L1 incident from the first half mirror 14 to exit therefrom toward the third half mirror 17 described above. Further, the second half mirror 15 and the second lens group 16 allow the corneal reflection light R3 incident from the third half mirror 17 to exit therefrom toward the first half mirror 14.

In this manner, the corneal surface of the cornea Ea is irradiated with, through the first lens group 18, the illumination light L1 emitted from the first illumination light source 11 and passing through the lens 12 and the third half mirror 17. As a result, the corneal reflection light R1, which is the reflection of the illumination light L1 from the corneal surface, enters the first lens group 18.

The corneal measurement optical system 1b forms an optical path branching from the first illumination optical system 1c via the first half mirror 14. The corneal measurement optical system 1b shares the components from the first lens group 18 to the first half mirror 14 with the first illumination optical system 1c, and also includes a diaphragm 21, a lens 22, and an interference image capturing camera 23.

The diaphragm 21 and the lens 22 allow the corneal reflection light R3 incident from the first half mirror 14 to exit therefrom toward the interference image capturing camera 23.

The interference image capturing camera 23 includes a CMOS or CCD imaging element, and takes an image of the corneal reflection light R3 incident from the lens 22 to output an imaging signal of a corneal reflection image to the control unit 10.

A fixation lamp 24 is a light source that fixes the position of the subject's eye E by guiding the subject's gaze for accurate observation and photographing of the state of the subject's eye E. A light emitting diode (LED) light source or a halogen lamp can be used as the fixation lamp 24. The light L2 emitted from the fixation lamp 24 passes through the second half mirror 15 and the second lens group 16, is reflected from the third half mirror 17, and enters the subject's eye E through the first lens group 18. Specifically, the subject's eye E can be irradiated with the light L2 from the fixation lamp 24 through the first lens group 18 included in an alignment adjustment system, which will be described later.

The alignment adjustment system is a mechanism including an alignment adjustment unit 40, such as a servo motor, that makes the first lens group 18 movable. Driving the servo motor electrically connected to the control unit 10 to move the first lens group 18 makes it possible to adjust the relative position between the subject's eye E and the first lens group 18 in an optical axis direction, and to adjust the alignment of the optical system. That is, the alignment of the light of the fixation lamp 24 irradiated through the first lens group 18 can also be adjusted at the same time. This allows the light L2 from the fixation lamp 24 to be focused on the fundus (retina) of the subject's eye E. Therefore, blurring, caused by the movement of an eyeball, of an image captured by, for example, the anterior segment camera 20 or blurring of an image captured by the interference image capturing camera 23 can be reduced while maintaining the focus on the anterior segment.

The alignment adjustment system is used for measuring the alignment of the subject's eye E and the first lens group 18 in the optical axis direction by an optical lever method. The alignment adjustment system performs an adjustment (alignment adjustment) of the relative position between the subject's eye E and the optical system by moving the first lens group 18 using the result of the alignment measurement. The alignment adjustment system includes a holder 25 integrally formed with an imaging lens 19a, an alignment light source 4a (alignment light emitting unit), which is located near the anterior segment camera 20, and an alignment reflection light receiving unit 4b, and can perform an alignment measurement. The alignment light source 4a and the alignment reflection light receiving unit 4b are integrated with, or fixed at a relative position to, the holder 25. This can improve the accuracy of alignment detection.

A ghost removing light source 4 may be, for example, a light emitting diode (LED) light source or a halogen lamp, and is able to emit illumination light L3 toward a corneal surface of a cornea Ea of a subject's eye E. The ghost removing light source 4 has an optical axis that is shifted from the optical axis of the first lens group 18, which will be described later (second illumination optical system 1d).

Figure 2:
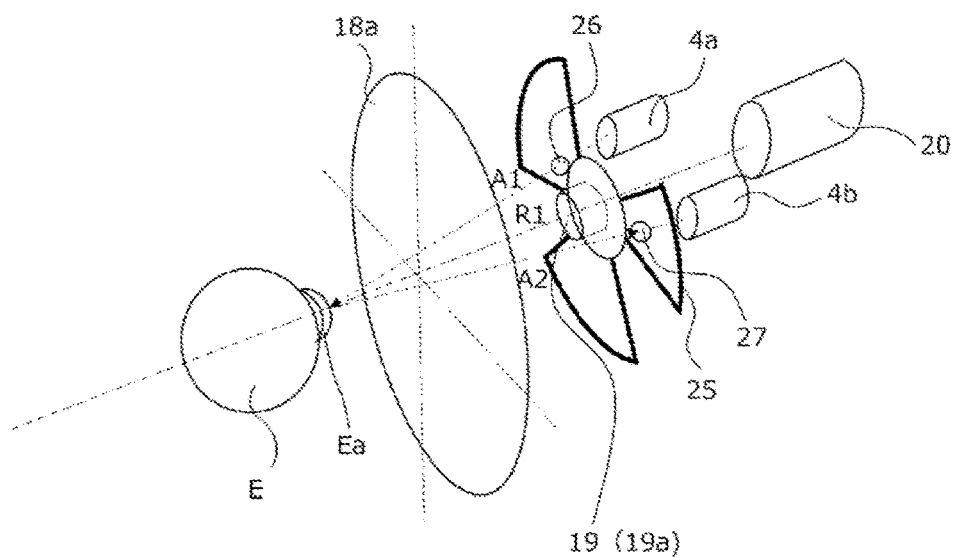
FIG. 2 is a perspective view illustrating a major part of the optical system of the ophthalmologic apparatus according to the first embodiment of the present disclosure.

FIG. 2 is a perspective view illustrating a major part of the optical system of the ophthalmologic apparatus according to the embodiment of the present disclosure. FIG. 2 illustrates, among the components of the anterior segment observation optical system 1a of the ophthalmologic apparatus according to the embodiment of the present disclosure, the subject's eye E, the alignment light source 4a, the alignment reflection light receiving unit 4b, an objective lens 18a, the anterior segment camera 20, and the holder 25 only. Note that the holder 25, the alignment light source 4a, the alignment reflection light receiving unit 4b, the anterior segment camera 20 are spaced apart in FIG. 2 so that their positional relationship can easily be understood. The holder 25 includes an imaging transmissive portion 19, and a first light-transmissive portion 26 and a second light-transmissive portion 27 for the alignment light source 4a. In FIG. 2, the imaging transmissive portion 19 includes the imaging lens 19a that transmits the corneal reflection light R3. The first light-transmissive portion 26 is an opening that is formed in the holder 25 and transmits alignment light A1 emitted from the alignment light source 4a. The second light-transmissive portion 27 is an opening that is formed in the holder 25 and transmits alignment reflection light A2. In this manner, the alignment light A1 emitted from the alignment light source 4a is transmitted by the first light-transmissive portion 26, and the alignment reflection light A2, which is the reflection from the cornea Ea of the subject's eye E, is transmitted by the second light-transmissive portion 27 and received by the alignment reflection light receiving unit 4b. As thus described above, the holder 25 is provided with the first and second light-transmissive portions 26 and 27 and the imaging transmissive portion 19, and the alignment light source 4a and the alignment reflection light receiving unit 4b are fixed to the holder 25. Hence, the holder 25, the alignment light source 4a, and the alignment reflection light receiving unit 4b can be handled as a single module. The alignment reflection light receiving unit 4b may be a linear sensor or an area sensor such as a CCD, a CMOS, and a PSD (position sensitive detector). Alternatively, the alignment reflection light receiving unit 4b may have a plurality of light-receiving regions.

Hereinafter, the details are described. The alignment light source 4a emits the alignment light A1. The alignment light A1 emitted passes the first light-transmissive portion 26 and enters the corneal surface of the cornea Ea in an oblique direction relative to the corneal surface via the first lens group 18. When the first lens group 18 is in appropriate alignment with the subject's eye E, the alignment reflection light receiving unit 4b can receive, at a predetermined position of the alignment reflection light receiving unit 4b, the alignment reflection light A2, which is the reflection from the surface of the cornea Ea, after the alignment reflection light A2 is transmitted by the second light-transmissive portion 27. That is, the alignment reflection light A2, which is the reflection from the surface of the cornea Ea, can be received by the alignment reflection light receiving unit 4b via the first lens group 18. The alignment reflection light receiving unit 4b outputs a light receiving signal indicative of the receipt of the alignment reflection light A2 to the control unit 10. Accordingly, whether the subject's eye E and the first lens group 18 are appropriately aligned or not can be determined by the control unit 10 based on the determination as to whether the alignment reflection light receiving unit 4b receives the alignment reflection light A2 at a certain appropriate position or not.

To improve the accuracy of alignment adjustment, it is important to set the relative position between the alignment light source 4a and the alignment reflection light receiving unit 4b accurately. The holder 25, the alignment light source 4a and the alignment reflection light receiving unit 4b can be handled as a single module. This can improve the accuracy of the relative position between the alignment light source 4a and the alignment reflection light receiving unit 4b. As thus the holder 25, the alignment light source 4a, and the alignment reflection light receiving unit 4b are configured as a single module, further downsizing is achievable compared with the case in which the holder 25, the alignment light source 4a, and the alignment reflection light receiving unit 4b are separately arranged.

Further, the holder 25 and the anterior segment camera 20 may be configured as a single module. In this case, the anterior segment camera 20 can be integrated with the alignment light source 4a and the alignment reflection light receiving unit 4b via the holder 25 to be a single module so that the alignment accuracy with respect to the anterior segment camera 20 can be further improved. Furthermore, in manufacturing the ophthalmologic apparatus 1, it is possible to reduce the burden on the steps for improving the installation accuracy of (the accuracy of the relative position among) the anterior segment camera 20, the alignment light source 4a, and the alignment reflection light receiving unit 4b.

The alignment adjustment system with a configuration in which the first lens group 18 is moved is described above. However, the relative position between the subject's eye E (person) and the ophthalmologic apparatus 1 may be made moved by moving the entire ophthalmologic apparatus 1. This movement is controlled by the control unit 10.

The control unit 10 detects, based on the inputted image data of the corneal reflection light R2 (corneal reflection image), wavelength characteristics of the interference image at each position of the corneal reflection image so that the thickness of the tear fluid film at each position on the corneal surface can be detected. The tear fluid film herein refers to an oil layer (lipid layer), an aqueous layer, and a mucinous layer, or a combination of these layers.

As described above, providing the holder 25 with the first and second light-transmissive portions 26 and 27 for the alignment light source makes it possible to handle the holder 25, the alignment light source 4a, and the alignment reflection light receiving unit 4b as a single module. This can contribute to the downsizing of the apparatus, while increasing the accuracy of alignment detection. As thus the accuracy of detection alignment can be enhanced, the anterior segment camera 20 can capture an image of the corneal reflection light R3 so that an accurate observation image of the anterior segment of the subject's eye E can be obtained. Further, it is possible to make the corneal reflection light R2, the image of which is captured by the interference image capturing camera 23, so as to accurately observe the interference fringes generated by the tear fluid film.

The imaging transmissive portion 19 may be formed as an opening in the holder 25, or may include a filter member that selectively transmits the corneal reflection light R3. Further, the first and second light-transmissive portions 26 and 27 may include a lens, or may include a filter member that selectively transmits light.

The first illumination light source 11 of the present disclosure is a light source made of a single LED. Therefore, even when the illumination light L1 emitted from the first illumination light source 11 reaches the cornea Ea through the first lens group 18, the shape of a single light source is projected.

In opposition to this, a comparative example will be described now where a plurality of light sources including nine LEDs arranged in a matrix of 3×3 are used as the first illumination light source 11, for example. Thus, when the illumination light emitted from the first illumination light source 11 of the comparative example reaches the cornea Ea through the first lens group 18, the light from the plurality of LEDs, i.e., point light sources, is condensed by the first lens group 18 to generate dark portions adjacent to the plurality of LEDs. That is, illuminance difference in the shape of stripes is projected on the cornea Ea as blurred stripes. Therefore, the stripes of the illuminance difference are also generated in the corneal reflection light R1 reflected from the cornea. As a result, the illumination on the cornea of the subject's eye has shades, and the thickness of the tear fluid on the corneal surface may not be accurately measured.

On the other hand, according to the present disclosure, measurement of the cornea is performed under illumination from a single light source. This makes it possible to accurately measure the thickness of the tear fluid on the corneal surface without generating the stripes of the illuminance difference on the cornea.

Further, the light L2 from the fixation lamp 24 is superimposed and irradiated via the first lens group that is an optical system of the alignment adjustment system, so that the blurring caused by the movement of the eyeball can be reduced by maintaining the focus state, and interference fringes formed by the tear fluid film of the cornea Ea of the subject's eye E can be accurately observed.

The control unit 10 can switch between the first illumination light source 11 and the ghost removing light source 4 (second illumination light source) to irradiate the eye with the illumination light. This enables switching between the mode for reducing ghost and the mode for irradiating the center of the subject's eye E with light in accordance with the examination to be performed.

Irradiating the illumination light L3 from the ghost removing light source 4 makes it possible to shift the position of ghost generated by reflection of the illumination light L3 at the anterior segment away from the optical axis of the anterior segment camera 20. In this manner, ghost can be kept from entering the field of view of the anterior segment camera 20. Hence, it is possible to perform an accurate examination of a cornea or tear fluid film around the center of a subject's eye E, and acquisition of a more accurate corneal image.

Figure 3:
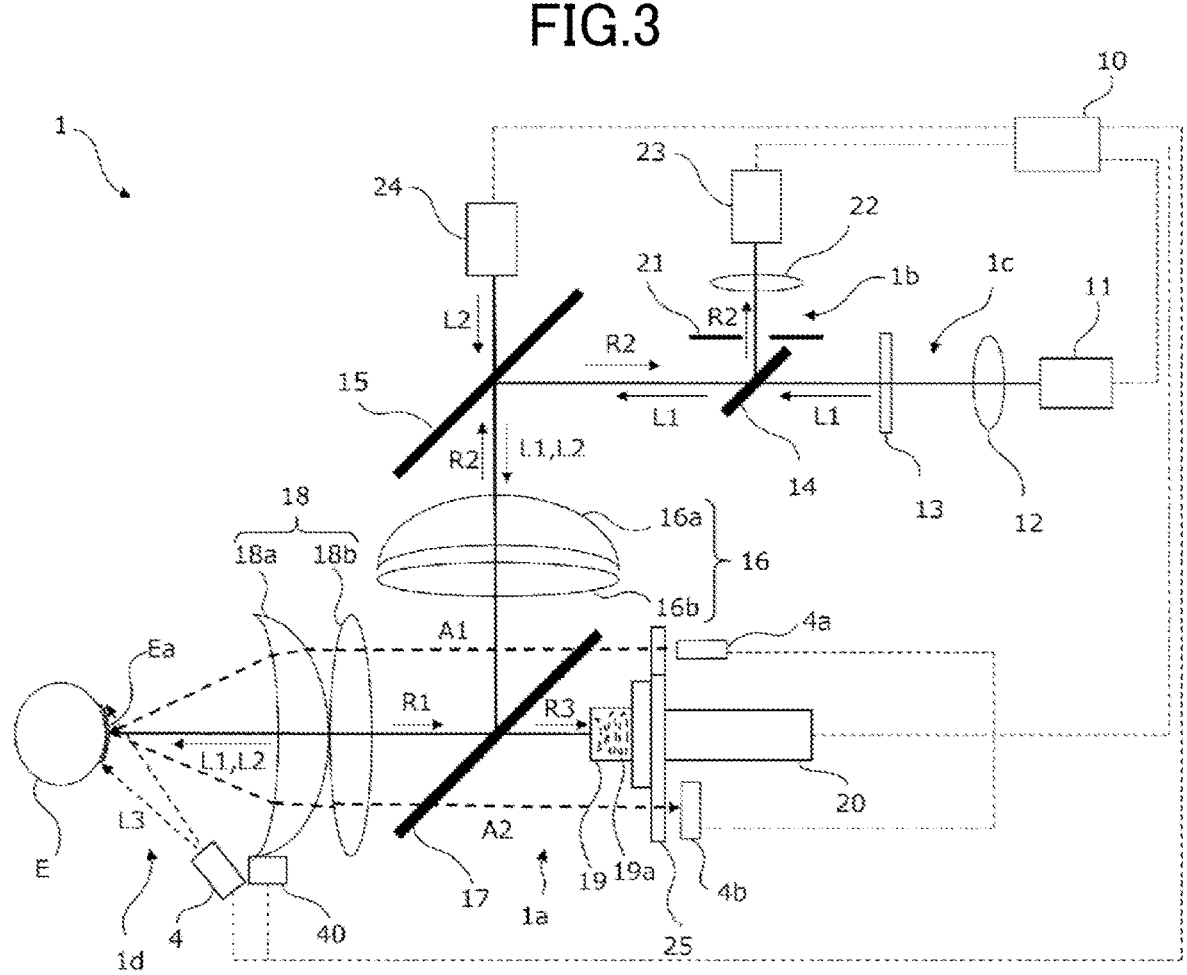
FIG. 3 is a schematic view showing an optical system of the ophthalmologic apparatus according to a variation of the first embodiment of the present disclosure.

Note that the ghost removing light source 4 (second illumination light source) from which the illumination light L3 is emitted may have an optical axis along which the illumination light L3 enters the cornea Ea of the subject's eye E from below as shown in FIG. 3. Alternatively, the ghost removing light source 4 may be arranged to have an optical axis that extends in a horizontal direction with respect to an optical axis center of the first lens group 18.

Second Embodiment

Figure 4:
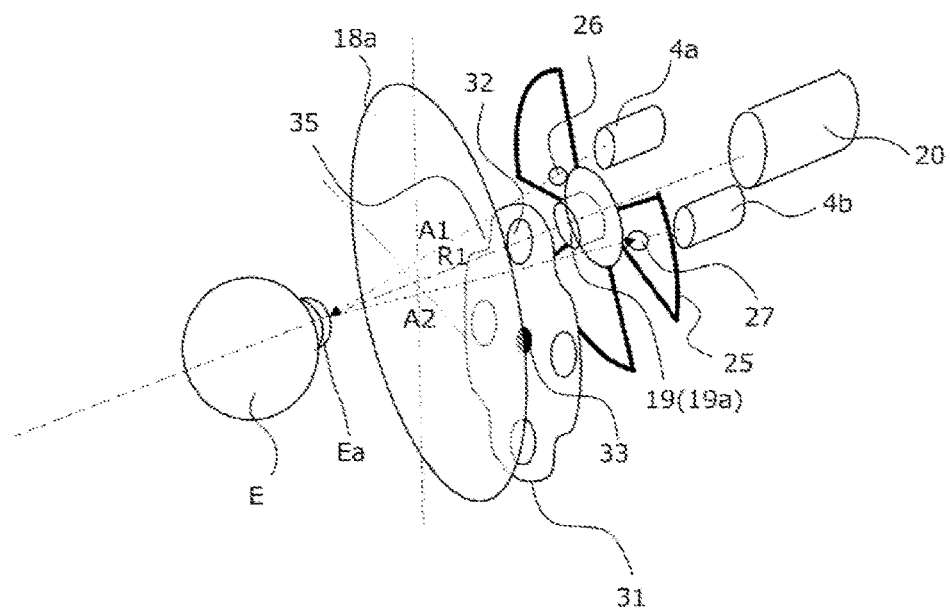
FIG. 4 is a perspective view illustrating a major part of an optical system of an ophthalmologic apparatus according to a second embodiment of the present disclosure.

FIG. 4 is a perspective view illustrating a major part of an optical system of an ophthalmologic apparatus 1 according to a second embodiment of the present disclosure. The second embodiment is different from the first embodiment in that a filter revolver 31 is arranged between the holder 25 and the objective lens 18a.

Figure 5:
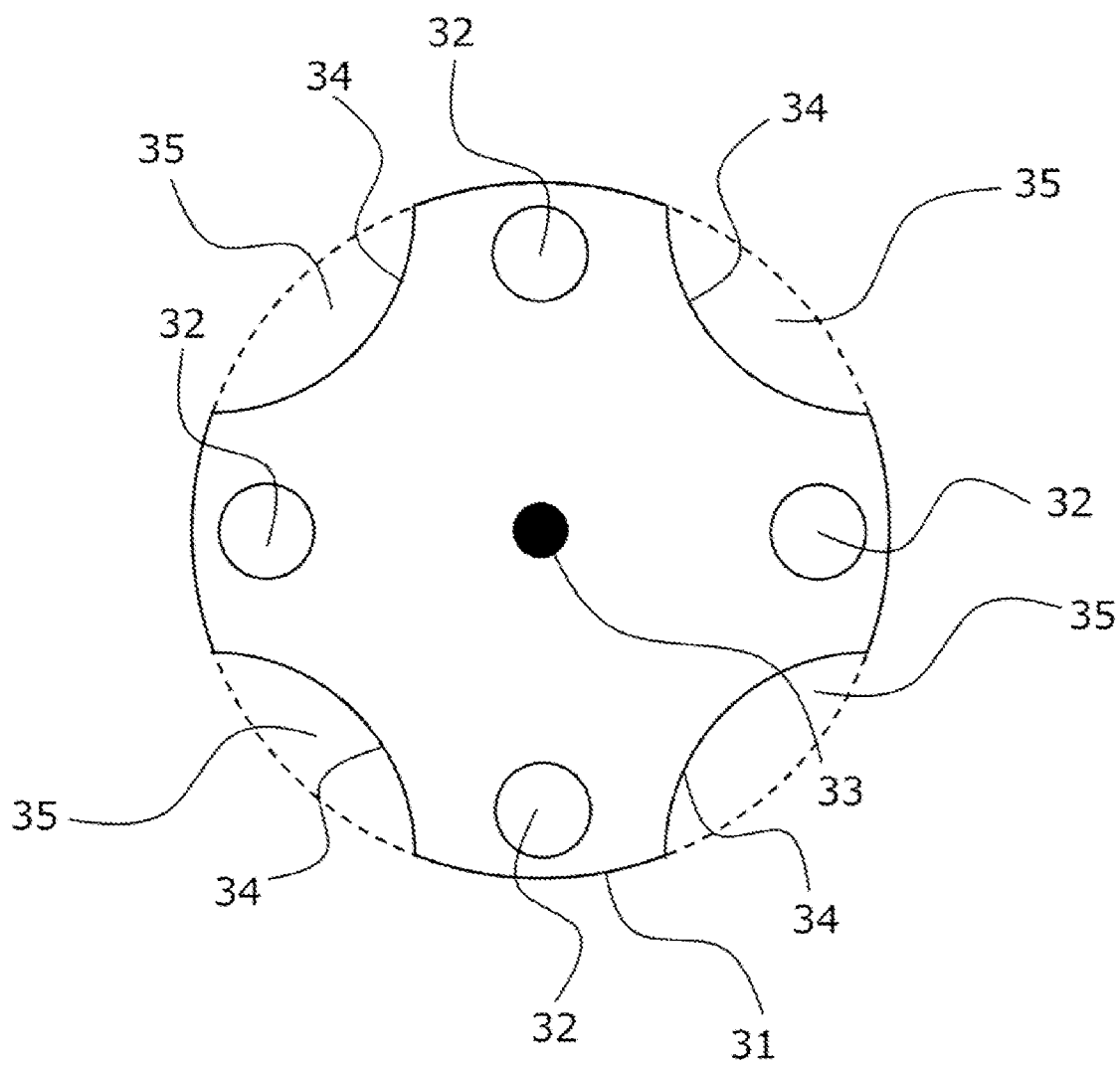
FIG. 5 is a schematic view illustrating a filter revolver according to the second embodiment of the present disclosure.

FIG. 5 is a schematic view illustrating the filter revolver 31 as viewed from the front. The filter revolver 31 is formed into a substantially cross shape with four corners cut out from a substantially circular shape (cut out portions 34). The filter revolver 31 has four types of imaging system filters 32 attached thereto, and can rotate about a rotation center 33. One of the four types of imaging system filters 32 is arranged on the optical axis of the imaging lens 19a. The four types of filters are configured to transmit lights of different wavelengths. The wavelength of the corneal reflection light R3 to be transmitted to the anterior segment camera 20 through the imaging lens 19a can be selected through the rotation of the filter revolver 31. The filter revolver 31 includes revolver transmissive portions 35 in the shape of cut out portions 34. Between the adjacent revolver transmissive portions 35, there is provided an imaging system filter 32. That is, the filter revolver 31 includes a plurality of cut out portions 34, and the imaging system filter 32 is arranged between at least two of the cut out portions 34. Note that the shape of the filter revolver 31 is not limited to the substantially cross shape; The filter revolver 31 may be formed into a substantially Y-shape or any other shape. Further, the number of types of the filters is not limited to four, and the number of the filter is not limited to four.

When the filter revolver 31 is viewed from the front in FIG. 4, the first and second light-transmissive portions 26 and 27 of the holder 25 respectively overlap with the revolver transmissive portions 35. Therefore, the alignment light emitted from the alignment light source 4a passes through the first light-transmissive portion 26 formed in a holder 25 and the revolver transmissive portion 35, and enters the corneal surface of the cornea Ea in an oblique direction as the alignment detection light A1 via the first lens group 18 (objective lens 18a). When the first lens group 18 is in alignment with the subject's eye E, the alignment reflection light receiving unit 4b receives alignment reflection light A2, which is the reflection of the alignment light from the cornea Ea, through the revolver transmissive portion 35 and the second light-transmissive portion 27. Specifically, the reflection of the alignment reflection light A2 from the cornea Ea can be received by the alignment reflection light receiving unit 4b via the first lens group 18. Accordingly, whether the subject's eye E and the first lens group 18 are aligned or not can be determined based on whether the alignment reflection light receiving unit 4b receives the alignment reflection light A2 or not.

As described above, in the filter revolver 31 including the imaging system filter 32, there are provided the revolver transmissive portions 35 respectively formed by the cut out portions 34 that transmit the alignment light A1 and the alignment reflection light A2. Hence, when the imaging system filter 32 is arranged on the optical axis of the imaging lens 19a and the anterior segment camera 20, the filter revolver 31 does not block the alignment light A1 and the alignment reflection light A2. Therefore, the filter revolver 31, the anterior segment camera 20, the alignment light source 4a, and the alignment reflection light receiving unit 4b can be brought close to each other, which makes it possible to downsize the entire apparatus.

DESCRIPTION OF REFERENCE CHARACTERS

1 Ophthalmologic Apparatus
1a Anterior Segment Observation Optical System
1b Corneal Measurement Optical System
1c First Illumination Optical System
1d Second Illumination Optical System 4 Ghost Removing Light Source
4a Alignment Light Source
4b Alignment Reflection Light Receiving Unit
10 Control Unit
11 Illumination Light Source
12 Lens
13 Filter
14 First Half Mirror
15 Second Half Mirror
16 Second Lens Group
17 Third Harf Mirror
18 First Lens Group
18a Objective Lens
19 Imaging Transmissive Portion
19a Imaging Lens
20 Anterior Segment Camera
21 Diaphragm
22 Lens
23 Interference Image Capturing Camera
24 Fixation Lamp
25 Holder
26 First Light-transmissive Portion
27 Second Light-transmissive Portion
31 Filter Revolver
32 Imaging System Filter
33 Rotation Center
34 Cut Out Portion
35 Revolver Transmissive Portion
40 Alignment Adjustment Unit

The invention claimed is:

1. An ophthalmologic apparatus, comprising:
an objective lens that faces a subject's eye;
an alignment light emitting unit that irradiates the subject's eye with alignment light to perform measurement of alignment between the objective lens and the subject's eye;
an alignment reflection light receiving unit that receives alignment reflection light, which is a reflection of the alignment light from the subject's eye;
an anterior segment camera that receives corneal reflection light; and
a holder positioned between the anterior segment camera and the objective lens to hold the anterior segment camera, wherein
the holder includes an imaging transmissive portion that transmits the corneal reflection light to the anterior segment camera, a first light-transmissive portion that transmits the alignment light from the alignment light emitting unit, and a second light-transmissive portion that transmits the alignment reflection light from the subject's eye, wherein the apparatus is further configured such that:
the alignment light passes the first light-transmissive portion and enters a corneal surface of the subject's eye in an oblique direction relative to the corneal surface via the objective lens,
the alignment reflection light passes the second light-transmissive portion and is received by the alignment reflection light receiving unit, via the objective lens,
the imaging transmissive portion and the anterior segment camera are arranged along a direction of an optical axis of the objective lens, and
the corneal reflection light enters the objective lens, passes the imaging transmissive portion and is received by the anterior segment camera.

2. The ophthalmologic apparatus of claim 1, wherein the holder, the alignment light emitting unit, and the alignment reflection light receiving unit are integrally formed.

3. The ophthalmologic apparatus of claim 1, wherein the holder constitutes the first light-transmissive portion and/or the second light-transmissive portion by a lens.

4. The ophthalmologic apparatus of claim 1, wherein the holder includes the first light-transmissive portion and/or the second light-transmissive portion formed as an opening.

5. The ophthalmologic apparatus of claim 1, wherein the holder includes a filter member that selectively transmits light in the first light-transmissive portion and/or the second light-transmissive portion.

6. The ophthalmologic apparatus of claim 1, wherein the holder and the anterior segment camera are integrally formed.

7. The ophthalmologic apparatus of claim 1, wherein the holder includes the imaging transmissive portion configured by a lens.

8. The ophthalmologic apparatus of claim 1, wherein the holder includes the imaging transmissive portion formed as an opening.

9. The ophthalmologic apparatus of claim 1, wherein the holder includes the imaging transmissive portion including a filter member that selectively transmits light.

10. An ophthalmologic apparatus, comprising:
an objective lens that faces a subject's eye;
an alignment light emitting unit that irradiates the subject's eye with alignment light to perform measurement of alignment between the objective lens and the subject's eye;
an alignment reflection light receiving unit that receives alignment reflection light, which is a reflection of the alignment light from the subject's eye;
an anterior segment camera that receives corneal reflection light;
a holder positioned between the anterior segment camera and the objective lens to hold the anterior segment camera; and
a filter revolver that is rotatably supported between the objective lens and the holder and includes a plurality of filters, wherein
the holder includes an imaging transmissive portion that transmits the corneal reflection light to the anterior segment camera, a first light-transmissive portion that transmits the alignment light from the alignment light emitting unit, and a second light-transmissive portion that transmits the alignment reflection light from the subject's eye, wherein
the holder includes the imaging transmissive portion including a filter member that selectively transmits light, and wherein
one of the plurality of filters of the filter revolver is capable of being in alignment with an optical axis of the anterior segment camera by rotation of the filter revolver, and
the filter revolver includes a plurality of cut out portions, and the one of the plurality of filters is arranged between at least two cut out portions.

11. An ophthalmologic apparatus, comprising:
an objective lens that faces a subject's eye;
an alignment light emitting unit that irradiates the subject's eye with alignment light to perform measurement of alignment between the objective lens and the subject's eye;

an alignment reflection light receiving unit that receives alignment reflection light, which is a reflection of the alignment light from the subject's eye;

an anterior segment camera that receives corneal reflection light;

a holder positioned between the anterior segment camera and the objective lens to hold the anterior segment camera; and a first illumination optical system that irradiates a cornea of the subject's eye with illumination light emitted from a first illumination light source along an optical axis overlapping an optical axis center of the objective lens, wherein the holder includes an imaging transmissive portion that transmits the corneal reflection light to the anterior segment camera, a first light-transmissive portion that transmits the alignment light from the alignment light emitting unit, and a second light-transmissive portion that transmits the alignment reflection light from the subject's eye, and wherein the first illumination optical system includes only a single light source.

12. The ophthalmologic apparatus of claim 11, wherein the single light source is bullet-shaped LED.

13. The ophthalmologic apparatus of claim 1, further comprising:

a first illumination light source that irradiates a cornea of a subject's eye with illumination light;

an alignment adjustment unit capable of adjusting a position of the objective lens for adjusting a relative position between the subject's eye and the objective lens, and a fixation lamp including a light source different from the first illumination light source, wherein the fixation lamp emits light that focuses on a retina of the subject's eye through the objective lens.

14. The ophthalmologic apparatus of claim 1, further comprising:

a first illumination optical system that irradiates a cornea of a subject's eye with illumination light emitted from a first illumination light source along an optical axis overlapping an optical axis center of the objective lens;

a second illumination optical system that irradiates the cornea of the subject's eye with illumination light emitted from a second illumination light source on an optical axis center different from the optical axis center of the objective lens; and a control unit that controls the first illumination light source and the second illumination light source, wherein the control unit switches between the first illumination light source and the second illumination light source to enable illumination light to be emitted.

15. The ophthalmologic apparatus of claim 14, wherein the second illumination light source emits illumination light to the cornea of the subject's eye without passing through the objective lens.

* * * * *